United States Patent [19]
Iyyalasomayazula

[11] Patent Number: 6,165,726
[45] Date of Patent: Dec. 26, 2000

[54] NON-RADIOACTIVE METHODS FOR CHEMICAL CLEAVAGE SEQUENCING AND FOOTPRINTING OF NUCLEIC ACIDS

[75] Inventor: Narayana Rao Iyyalasomayazula, Oak Ridge, Tenn.

[73] Assignee: UT-Battelle, LLC, Oak Ridge, Tenn.

[21] Appl. No.: 09/400,046

[22] Filed: Sep. 21, 1999

[51] Int. Cl.$^7$ .................................................. C12Q 1/68
[52] U.S. Cl. ............................................................. 435/6
[58] Field of Search ................................ 435/6, 7.5, 405, 435/91.53; 436/94

[56] References Cited

PUBLICATIONS

Isola et al. "Chemical Cleavage Sequencing of DNA Using Matrix–Assisted Laser Desorption/Ionization Time–of–Flight Mass Spectrometry" *Analytical Chemistry*, 71(13):2266–2269, 1999.

Ohara and Ohara. "A New Solid–Phase Chemical DNA Sequencing Method Which Uses Streptavidin–Coated Magnetic Beads" *DNA Research*, 2:123–128, 1995.

Rosenthal, A. "DNA Sequencing by Chemical Degradation Using One, Two, and Four Different Fluorophores" *Methods in Mol. Biol.* 23:261–280, 1993.

Richterich, P. Non–Radioactive Chemical Sequencing of Biotin Labeled DNA. *Nucleic Acids Research*, 17(6):2181–2186, 1989.

Maxam and Gilbert. "A New Method for Sequencing DNA" *Proc Natl Acad Sci USA*, 74(2):560–564, Feb. 1977.

Ohara et al., "Automated Fluorescent DNA Sequencing by a Simplified Solid–Phase Chemical Sequencing Method," Biotechniques, 1997, vol. 22, No. 4, 1997.

Bassam et al., "DNA amplification fingerprinting of bacteria," Applied Microbiology Biotechnology, 1992, vol. 38, pp. 70–76.

Ikuta et al., "Reverse–Phase Polystyrene Column for Purification and Analysis of DNA Oligomers," Analytical Chemistry, 1984, vol. 56, pp. 2253–2256.

Theisen et al., "Fluorescent dye phosphoramidite labelling of oligonucleotides," Nucleic Acids Symposium Series, 1992, vol. 27, pp. 99–100.

*Primary Examiner*—John S. Brusca
*Assistant Examiner*—Young Kim
*Attorney, Agent, or Firm*—Needle & Rosenberg, PC

[57] ABSTRACT

A method of sequencing a nucleic acid is provided, comprising: a) labeling the nucleic acid with biotin; b) subjecting the nucleic acid of step a) to base specific chemical modifications; c) cleaving the nucleic acid of step b) at the modified bases with hot piperidine; d) contacting the nucleic acid of step c) with immobilized streptavidin, whereby biotin-containing fragments are bound to immobilized streptavidin and unbound fragments are washed off; e) extracting the streptavidin bound fragments of step d); f) resolving the fragments of step e) on a denaturing polyacrylamide gel; and g) staining the fragments in the gel of step f) by silver staining. A further method of sequencing a nucleic acid is provided, comprising a) labeling the nucleic acid with DMT (dimethyl trityl protective group); b) subjecting the nucleic acid of step a) to base specific chemical modifications; c) cleaving the nucleic acid of step b) at the modified bases with hot piperidine; d) contacting the nucleic acid of step c) with an OPC (Oligo Purification Column) whereby DMT-containing fragments are bound to the OPC and unbound fragments are washed off; e) eluting the fragments that bound to the OPC in step d); f) resolving the fragments of step e) on a denaturing polyacrylamide gel; and g) staining the fragments in the gel of step f) by silver staining. Methods for DNAse I footprinting, footprinting with Exonuclease III, hydroxyl radical footprinting, methylation protection and methylation interference studies and ethylation protection studies are provided. Kits containing some or all of the components needed to practice one or more steps of the present method are provided.

2 Claims, 3 Drawing Sheets

B-TACTCCCCTGCCCTCCACAAGATGTTTTGC (SEQ ID NO:1);   Template

B-TACTCCCCTGCCCTCCACAAGATGTTTTGC (SEQ ID NO:2);
B-TACTCCCCTGCCCTCCACAAGATGTTTC (SEQ ID NO:3);    Products of the G
B-TACTCCCCTGCCCTCCACAAGATTTTGC (SEQ ID NO:4);    reaction
B-TACTCCCCTGCCCTCCACAAATGTTTGC (SEQ ID NO:5);    (Total products)
B-TACTCCCCTCCCTCCACAAGATGTTTTGC (SEQ ID NO:6)

B-TACTCCCCTGCCCTCCACAAGATGTTTTGC (SEQ ID NO:7);
B-TACTCCCCTGCCCTCCACAAGATGTTTT (SEQ ID NO:8);    Products of the G reaction
B-TACTCCCCTGCCCTCCACAAGAT (SEQ ID NO:9);         captured by the beads
B-TACTCCCCTGCCCTCCACAA (SEQ ID NO:10);           (Informative products)
B-TACTCCCCT (SEQ ID NO:11)

Fig. 1

NON-RADIOACTIVE METHODS FOR CHEMICAL CLEAVAGE SEQUENCING AND FOOTPRINTING OF NUCLEIC ACIDS

BACKGROUND OF THE INVENTION

1. Field of the Invention

The invention relates to sequencing methods that permit direct detection of nucleic acid fragments on a sequencing gel. More specifically, silver staining can be used to stain the sequencing gel and thereby provide a record of the nucleic acid fragments for sequence determination.

2. Background Art

Prior art sequencing methods utilize radioactive or fluorescent labels to visualize DNA fragments to determine the sequence of the nucleic acid. Some prior art methods have used biotin labeled DNA for chemical sequencing, and involve transfer of the DNA from the gel to a membrane, which is not only cumbersome but also expensive (the large size membranes required for handling sequencing gels are expensive). The present method of affinity purification of the fragments is rapid and avoids the need for transfer to a membrane while providing a permanent record of a silver stained gel.

SUMMARY OF THE INVENTION

A method of sequencing a nucleic acid is provided, comprising: a) labeling the nucleic acid with biotin; b) subjecting the nucleic acid of step a) to base specific chemical modifications; c) cleaving the nucleic acid of step b) at the modified bases with hot piperidine; d) contacting the nucleic acid of step c) with immobilized streptavidin, whereby biotin-containing fragments are bound to immobilized streptavidin and unbound fragments are washed off; e) extracting the streptavidin bound fragments of step d); f) resolving the fragments of step e) on a denaturing polyacrylamide gel; and g) staining the fragments in the gel of step f) by silver staining.

A further method of sequencing a nucleic acid is provided, comprising: a) labeling the nucleic acid with DMT (dimethyl trityl protective group); b) subjecting the nucleic acid of step a) to base specific chemical modifications; c) cleaving the nucleic acid of step b) at the modified bases with hot piperidine; d) contacting the nucleic acid of step c) with an OPC (Oligo Purification Column) whereby DMT-containing fragments are bound to the OPC and unbound fragments are washed off, e) eluting the fragments that bound to the OPC in step d); f) resolving the fragments of step e) on a denaturing polyacrylamide gel; and g) staining the fragments in the gel of step f) by silver staining.

BRIEF DESCRIPTION OF THE FIGURES

FIG. 1 is a schematic of the present biotin capture method for chemical cleavage sequencing.

DETAILED DESCRIPTION OF THE INVENTION

Figure 2A:
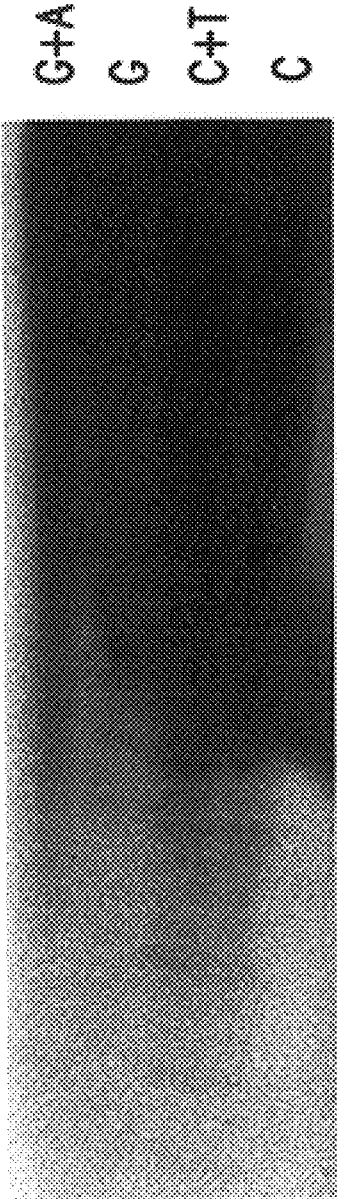
FIG. 2 shows the of the Biotin capture chemical cleavage sequencing resolved on 12% denaturing Acrylamide gel. Panel A represents the total fragments of the G+A, G, C+T and C reactions. Panel B represents the end fragments sorted by magnetic beads providing a readable sequence.

A method of sequencing a nucleic acid is provided, comprising: a) labeling the nucleic acid with biotin; b) subjecting the nucleic acid of step a) to base specific chemical modifications; c) cleaving the nucleic acid of step b) at the modified bases with hot piperidine; d) contacting the nucleic acid of step c) with immobilized streptavidin, whereby biotin-containing fragments are bound to immobilized streptavidin and unbound fragments are washed off; e) extracting the streptavidin bound fragments of step d); f) resolving the fragments of step e) on a denaturing polyacrylamide gel; and g) staining the fragments in the gel of step f) by silver staining. This method consists briefly of the steps described below. The principle of this method is illustrated in FIG. 1).

The nucleic acid to be analyzed (sequence determination, footprinting, DNAse hypersensitivity determination, etc.) is initially labeled with biotin at one end of the molecule. This can be readily achieved by using a biotin labeled primer in PCR amplification of required target sequence for analysis. An example of a detailed protocol for a biotin labeling step for use in chemical sequencing is described in Ohara and Ohara (Nucleic Acids Research 16:3025–3038, 1995). An example of chemical modification of bases for sequencing purposes is described in Maxam and Gilbert (Proc Natl Acad Sci USA 74(2):560–564, 1997).

The nucleic acid is subjected to base specific chemical modifications (purine, pyrimidine, cytosine, guanine reactions) as described by Maxam and Gilbert.

The nucleic acid is cleaved at the modified bases. An example of a detailed protocol for a cleavage step of the present invention using hot piperidine is described in Maxam and Gilbert. There are other methods such as hydroxyl radicals which cleave uniformly (Tullius, Th. D. and Dombroski, B. A. Science 230:679–681, 1985; and Cons, B. M. G. and Fox. K. R. Nucleic Acids Research 17:5447–5459, 1989). Piperidine is preferred as it is a reliable method which cleaves the modified bases and has been shown to be effectively used for this purpose. Similarly, formamide can be used for cleavage of the bases, and the sequences are analyzed directly based on the size differences etc. (Negri. R., Costanzo,G. and Di Mauro, E. Anal Biochem 197:389–395, 1991). The present methods using either the biotin or DMT (described below) can be readily used with formamide cleavage.

The biotin containing fragments are captured by immobilized streptavidin (streptavidin linked magnetic beads, membranes, etc.) and the unbound fragments are washed off. An example of a detailed protocol for the use of immobilized streptavidin to capture biotin labeled nucleic acids is provided in Ohara and Ohara. Other forms of immobilized streptavidin can also be used, for example membrane-bound streptavidin, such as SAM Streptavidin membranes (Boeringher-Mannheim Corporation), which is a membrane coated with Streptavidin with a high binding capacity and is suitable for use with this application. Streptavidin coated microtiter plates are also available from this company. Currently Xenopore (Hawthorne, N.J.) provides streptavidin coated slides and cover slips. All these solid surfaces should be optimized since the binding capacities are different. However, with minimal amount of optimization an inexpensive alternative to the magnetic beads method could readily be found. These flat surfaces offer an addition advantage of being able to multiplex the reactions. Briefly, the samples to be analyzed can be spotted and bound to these surfaces prior to performing the cleavage reactions and several samples can be processed simultaneously.

The streptavidin bound (informative) fragments are extracted and the resulting products are resolved on a denaturing polyacrylamide gel (sequencing gel). For extracting the streptavidin bound fragments ammonium hydroxide can be used as described (Jurinke, C., van den Boom, D., Collazo, V., Luchow, A., Jacob, A., and Koster, H. Analytical Chemistry 904–907, 1997.). Alternatively, hot phenol can be used as previously described (Lee, Y-H. and Vacquier, V. D. Analytical Biochemistry 206:206–207, 1992), or formaldehyde can be used as previously described (Tong, X. and Smith L. M. Analytical Chemistry 64:2672–2677, 1992) An example of a method of resolving the nucleic acid fragments in a sequencing gel are provided by Maxam and Gilbert. Further examples of such an experiment using a 12% polyacrylamide gel is provided in FIG. 2 and FIG. 3.

Figure 2B:
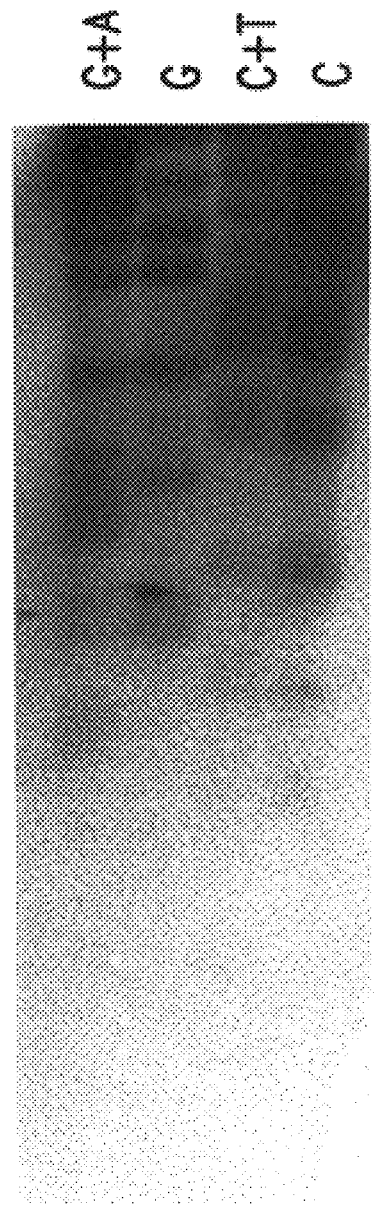

The present method takes the unique approach of silver staining the reaction products in a sequencing gel prepared as described above. For example, the present highly sensitive silver staining procedure can be performed using Seequence Silver Staining Kit from Promega corporation (Madison, Wis.) in accordance with the manufacturer's instruction. This recently introduced kit is considerably more sensitive compared to the other silver staining kits available in the market. By this method the nucleic acid fragments can be visualized directly in the silver stained sequencing gel. This step has the very important advantage of negating the need for the costly and time consuming blotting procedures used in current sequencing methods. This method has the additional advantage of providing a permanent record of the gel which is highly informative especially when performing footprinting, methylation interference assays and chemical nuclease analysis (results are shown in FIG. 2).

A further method of sequencing a nucleic acid is provided, comprising: a) labeling the nucleic acid with DMT (dimethyl trityl protective group); b) subjecting the nucleic acid of step a) to base specific chemical modifications; c) cleaving the nucleic acid of step b) at the modified bases with hot piperidine; d) contacting the nucleic acid of step c) with an OPC (Oligo Purification Column) whereby DMT-containing fragments are bound to the OPC and unbound fragments are washed off; e) eluting the fragments that bound to the OPC in step d); i) resolving the fragments of step e) on a denaturing polyacrylamide gel; and g) staining the fragments in the gel of step f) by silver staining.

Dimethyl trityl is a protective group on the nucleosides used during synthesis of oligonucleotides. All commercial DNA synthesizers are equipped with an option trityl on or trityl off synthesis mode. This means the trityl group (DMT) is either left intact or removed from the last (i.e., 5' end) base. When very high purity is required for the oligonucleotide (depending on the use) the synthesis is performed with trityl on and then the product is purified using the OPC columns. For example if a 20 base oligo is being synthesized only the final product (20 mer) will have a trityl at the end and other failure sequences (19,18,17 etc) will not. Using the OPC column which selectively binds to the DMT will purify the 20 mer from the remaining oligos. Most companies will provide oligonucleotides with trityl on for no additional charge. Alternatively, DMT-labeled nucleic acids can be prepared by preparing primers with DMT on the last (5') base.

The method using DMT is briefly as follows. Prepare polymerase chain reaction amplification products of the target to be sequenced using two primers (one of them with the trityl on). Perform chemical cleavage reactions of the target using Maxam Gilbert chemistry. Resuspend the final products in water and pass them through an activated OPC column (Oligo Purification Cartridge). Activation of the OPC resin is performed by passing acetonitrile through the column. The DNAs containing the trityl group are bound to the column. The columns are washed with 1.5 M ammonium hydroxide solution. This step will make the initial double stranded DNA into single stranded form and remove all the fragments which do not contain trityl groups. Thus only the end fragments containing trityl will be left on the column matrix. These are eluted into acetonitrile. Acetonitrile is removed by evaporation and the DNA fragments are resuspended in aqueous buffer for loading onto the sequencing gels. This method can readily be modified to use the column resin in pipette tips for easy manipulation and multiplexing.

The cleavage step, elution step and resolution step are as described above. The product capture step for the DMT-labeled nucleic acids involves binding the DMT specifically to OPC (Oligo Purification Cartridge) columns as has been described for other applications such as oligonucleotide purification, etc. The final key step of silver staining the gel is the same regardless of the label or capture molecules used.

Because of the advantages of the present method, it can be applied to footprinting protocols and other applications for DNA-protein interaction analysis methods.

For example, the study of protein-nucleic acid interactions is currently one of the most rapidly growing areas of molecular biology. DNA (RNA) binding proteins are at the heart of gene regulation, expression, splicing, recombination and replication. Three key aspects of molecular genetics, replication, recombination and repair, all involve nucleic acid binding proteins. Current methods of analysis of DNA/protein interactions involve the use of radiolabeled nucleic acids. Several fluorescence based methods have been described in the literature. However, these methods have the disadvantage that they require the use of automated DNA sequencers to analyze the reactions.

This invention provides a non-radioactive method which can be used in a conventional molecular biology laboratory for the study of DNA/protein interactions. Using previous methods, the binding experiments require the use of double stranded DNA. The double stranded DNA is asymmetrically labeled (i.e. one strand is end labeled, e.g., with $^{32}$P or $^{35}$S). The basic principle in these previous methods is that the binding of substances to specific sequences renders them either resistant or inaccessible to the cleavage reagents. The cleavage is performed in several different ways, with exonuclease cleavage, DNAseI cleavage and hydroxyl radical cleavage being typical examples. After the cleavage, the reaction products are resolved on denaturing gels and autoradiographed. The asymmetric labeling of the DNA fragments allows the detection of fragments from only one strand. However, when direct DNA staining methods such as silver stain have been employed this is not possible.

In the present invention, the use of biotin or DMT (dimethyl trityl) as a handle solves this problem by allowing simple purification of the labeled fragments, which will facilitate capturing the fragments containing the tag (biotin, DMT or other) and analysis directly by silver staining of the gel. Specific examples of methods in which the present technique can be used include DNAse I footprinting, footprinting with Exonuclease III, hydroxyl radical footprinting, methylation protection and methylation interference studies and ethylation protection studies. These methods are well known in the art as illustrated by methods described below.

Protocols for DNAse I footprinting, which can use the approach of the present invention include: Leblanc B and Moss T. 1994 DNAse I Footprinting DNA-Protein Interactions: Principles and Protocols: Methods in Molecular Biology Ed G. G. Kneale. Humana Press, Totowa, N.J.; Schmitz, A. and Galas, D. J. 1978. DNAse I footprinting: a simple method for the detection of protein-DNA binding specificity. Nucleic Acids Research 5:3157–3170; and Brenowitz, M., Senear, D. F., and Kingston, R. E. 1991. DNase footprint analysis of protein-DNA binding, in Current Protocols in Molecular Biology (Ausubel, F. M., Brent, R., Kingston, R. E., Moor, D. E., Smith, S. A., and Struhl, K. Eds.), Greene and Wiley-Interscience, New York, pp. 12.4.1–12.4.11.

Protocols for footprinting with Exonuclease III which can use the approach of the present invention include: Metzger, W. and Heumann, H. 1994 Footprinting with Exonuclease III in DNA-Protein Interactions: Principles and Protocols: Methods in Molecular Biology Ed. G. G. Kneale. Humana Press, Totowa, N.J.; Shalloway, D., Kleinberger, T., and Livingston, D. M. 1980 Mapping of SV40 DNA replication origin region binding sites for the for the SV40 DNA replication antigen by protection against Exonuclease III digestion, Cell 20:411–422; and Wu, C. 1985 An exonuclease protection assay reveals heat-shock element and TATA box binding proteins in crude nuclear extracts. Nature 317:84–87.

Protocols for hydroxyl radical footprinting which can use the approach of the present invention include: Schickor, P and Heumann Hydroxyl Radical Footprinting. In DNA-Protein Interactions: Principles and Protocols: Methods in Molecular Biology Ed. G. G. Kneale. Humana Press, Totowa, N.J.; Chalepakis, G and Beato, M 1989 Hydroxyl radical interference: a new method for the study of protein-DNA interaction. Nucleic Acids Research 17: 1783; and Hayes, J. J. and Tullius, Th. D. 1989 The missing nucleoside experiment: a new technique to study recognition of DNA by protein. Biochemistry 28:9521–9527.

Protocols for methylation protection and methylation interference which can use the approach of the present invention include: A. Shaw, P. E., and Stewart A. F. Identification of Protein-DNA contacts with Dimethyl Sulfate. Methylation Protection and Methylation interference. In DNA-Protein Interactions: Principles and Protocols: Methods in Molecular Biology Ed G. G. Kneale. Humana Press, Totowa, N.J.; Church G. M. and Gilbert W. 1984 Genomic Sequencing. Proc Natl Acad Sci USA 81: 1991–1995; and Gilbert, W., Maxam, A., and Mirzabekov, A. 1976 Contacts between the LAC repressor and DNA revealed by methylation, in control of Ribosome Biosynthesis, Alfred Benzon Symposium IX (Kjelgaard, N. O. and Maaloe, O., Eds.) New York, pp 139–148.

Protocols for ethylation interference which can use the approach of the present invention include: Manfield I. and Stockley. P. G. Ethylation Interference in DNA-Protein Interactions: Principles and Protocols: Methods in Molecular Biology Ed G. G. Kneale. Humana Press, Totowa, N.J.; Bushman, F. D., Anderson, J. E., Harrison, S. C. and Ptashne, M. 1985 Ethylation interference and X-ray crystallography identify similar interactions between 434 repressor and operator. Nature 3:651–653; and Ptashne, M. 1987 A Genetic Switch: Gene Control and Phage Lambda. Blackwell Scientific, Boston, Mass.

The present invention also provides kits for use in sequencing and other molecular biology techniques as described herein. Once the method is describe, it is routine to formulate a kit to be used in the practice of the method.

For example a footprinting kit is provided. For a biotin-based system, the kit can contain the following components:

1. 20 µl of AP2 Extract
2. 0.3 µg SV40 Positive control DNA
3. 1,000 u RQ1 Rnase free DNAse
4. 5 ml Stop solution
5. 1.5 ml 10 mM Tris-HCl (pH 8.0)
6. 3 ml Ca2+/Mg2+ Solution
7. 1.5 ml Binding Buffer
8. Set of four primers for the control SV40 DNA amplification. One set with biotin at the 5' end and one set without
9. 2.0 ml Streptavidin magnetic beads (or streptavidin agarose)
10. 0.5 ml Loading solution Other versions of the present kit may include one or more of the following components:

1. 20 µl of AP2 Extract
2. 0.3 µg SV40 Positive control DNA
3. 5,000 u HindIII
4. 1 ml Restriction 1× Buffer E
5. 1,000 u Alkaline Phosphatase, Calf Intestinal (CIAP)
6. 200 u T4 Polynucleotide Kinase (PNK)
7. 100 µl Kinase 10× Buffer
8. 1,000 u RQ1 Rnase Free DNAse
9. 5 ml Stop solution
10. 1.5 ml 10 mM Tris-HCl (pH 8.0)
11. 3 ml Ca2+/Mg2+ Solution
12. 1.5 ml Binding Buffer
13. 0.5 ml Loading solution Kits for sequencing are also included. These would contain all or some of the reagents described herein for the present sequencing methods using biotin or DMT. The components for sequencing gels and silver stain are commercially available reagents.

It will be understood by the skilled artisan that the kit will preferably also contain a set of instructions at a level of detail appropriate to the skilled person. The protocols to be included will in most cases follow the protocols in the literature for the relevant methods as well as those described herein.

EXAMPLES

Example 1

10 micrograms of the biotin labeled DNA was used for C and G reactions while 20 micrograms was used for G+A and C+T reactions. The reactions were performed as described by Maxam and Gilbert for base specific modifications and cleavage. After cleavage the reaction mixtures were dissolved in 100 microliters Binding/Wash buffer (supplied by CPG inc Lincoln Park, N.J.). Ten microliters of Streptavidin magnetic beads (100 micrograms of beads suspended in aqueous solution) were added to each of the reactions. This amount of beads was selected arbitrarily, suggesting that fewer beads will be sufficient. The beads were collected to the side of a microfuge tube and the solution (containing uninformative fragments) was discarded. The beads were washed twice in Binding/wash buffer and once in 100% ethanol and were air dried.

Elution of the fragments from the beads was accomplished as follows: 100 microliters of Ammonium hydroxide (30% solution) was added to the tubes and the tubes were incubated at 65° C. for 10 minutes. The tubes were briefly chilled after this (to avoid overflow of the hot ammonia solution when the caps are opened) and the beads were held to a side of the tube using a magnet and the ammonia was removed into a fresh tube and dried. The biotin-containing DNA fragments were resuspended in 5 microliters of distilled water, 5 microliters of standard sequencing gel loading buffer (Sambrook et al., *Molecular Cloning: A Laboratory Manual*, 2and Ed., Cold Spring Harbor Laboratory, Cold Spring Harbor, N.Y., 1989) was added, and the mixture was heated at 95° C. for 2 minutes before loading on the gel. Typically one microliter of the mixture was electrophoresed on a 12% denaturing (sequencing) acrylamide gel in Tris Borate buffer at 2000 volts. After electrophoresis the gels were stained using the Promega Seequence silver staining kit.

The results of this sequencing method are shown in FIG. 2.

Example 2: P53 Protocol

Primer 1: 5'-GGATCCATCTGTTCACTTGTGCCCTG-3' (SEQ ID NO: 12)

Primer 2: 5-Biotin-GAATTCAACCAGCCCTGTCGTCTCTC-3' (SEQ ID NO: 13)

The two primers were designed to amplify a 274 base pair region corresponding to the Exon 5 of human p53 tumor suppressor gene. PCR amplifications were performed in 10 mM Tris-HCl buffer pH 8.3 containing 50 mM KCl, 1.5 mM $MgCl_2$, 0.1% Triton X-100, and 2.0 mM dNTPs (dATP, dCTP, dGTP, and dTTP). 100 nanograms of human genomic DNA from cell line K 562 was used as template, and the primers 1 and 2 (1 microgram each) were used in each of 50 microliter reactions. Amplifications were performed using 2.5 Units of Taq DNA polymerase. DNA was amplified for 40 cycles (1 min 95° C., 1 min 55° C., 1 min 72° C.) in an automated DNA thermal cycler (Amplitron II from Thermolyne). Ten microliters of the amplified product was analyzed on a 1% Agarose gel and the presence of the expected product was confirmed. Eight such reactions (50 microliters each) were pooled and the total DNA was concentrated before subjecting them to chemical cleavage sequencing as follows. The DNA was extracted once with phenol and precipitated with ethanol. The concentrated product was dissolved in 100 μl of sterile distilled water and 10 μl (for C and G reactions) or 20 μl (for G+A and C+T reactions) were used to perform the chemical cleavage sequencing using Maxam- Gilbert chemistry. After chemical cleavage the reaction products were resuspended in 100 microliters of binding buffer and 10 μl (100 micrograms) of streptavidin coated magnetic beads were added to each reaction and the biotin containing fragments were allowed to bind by incubation at room temperature for 5 minutes. The beads were held to the side of the microfuge tube with a magnet and the supernatant was removed using a pasteur pipette.

Since the template used was double stranded DNA an additional step involving denaturation was performed as follows. 200 μl of 0.1 N sodium hydroxide was added into each reaction and the DNA strands were allowed to dissociate. During this process the biotin containing strand remains attached to the beads and the complement is dissociated into solution. The solution was removed and the beads were washed twice with binding/wash buffer once with ethanol and were air dried. The streptavidin-biotin complex was dissociated by heating the samples in 30% ammonium hydroxide and the solution containing the DNA fragments was collected into fresh tubes and the ammonium hydroxide was evaporated to dryness in a speed-vac. The DNA fragments were dissolved in 5 microliters of sterile distilled water and 5 microliters of sequencing buffer was added. 1–2 microliters of this reaction was subjected to gel electrophoresis on a 6% denaturing sequencing gel and visualized by silver staining.

Schematic of the biotin capture method for double stranded templates is shown below:

```
B-gATCgATCgATCgATCgATC  (SEQ ID NO: 14)  Template
    CTAgCTAgCTAgCTAgCTAg  (SEQ ID NO: 15)

B-gATCgATCgATCgATC ATC  (SEQ ID NO: 16)
    CTAgCTAgCTAgCTAgCTAg  (SEQ ID NO: 17)
```

```
B-gATCgATCgATC ATCgATC      (SEQ ID NO: 18)
  CTAgCTAgCTAgCTAgCTAg       (SEQ ID NO: 19)

B-gATCgATC ATCgATCgATC      (SEQ ID NO: 20)  Products of the G Recation
  CTAgCTAgCTAgCTAgCTAg       (SEQ ID NO: 21)  (Total products)

B-gATC ATCgATCgATCgATC      (SEQ ID NO: 22)
  CTAgCTAgCTAgCTAgCTAg       (SEQ ID NO: 23)

B-ATCgATCgATCgATCgATC       (SEQ ID NO: 24)
  CTAgCTAgCTAgCTAgCTAg       (SEQ ID NO: 25)

B-gATCgATCgATCgATC          (SEQ ID NO: 26)
  CTAgCTAgCTAgCTAgCTAg       (SEQ ID NO: 27)

B-gATCgATCgATC              (SEQ ID NO: 28)
  CTAgCTAgCTAgCTAgCTAg       (SEQ ID NO: 29)

B-gATCgATC                  (SEQ ID NO: 30)  Products of the G Reaction
  CtAgCTAgCTAgCTAgCTAg       (SEQ ID NO: 31)  Captured on the beads B-gATC                      (SEQ ID NO: 32)
  CTAgCTAgCTAgCTAgCTAg       (SEQ ID NO: 33)

B-

B-gATCgATCgATCgATC          (SEQ ID NO: 34)

B-gATCgATCgATC              (SEQ ID NO: 35)  Products of the G Reaction
                                              After Sodium hydroxide treatment B-gATCgATC                  (SEQ ID NO: 36)

B-gATC                      (SEQ ID NO: 37)

B
```

Figure 3:
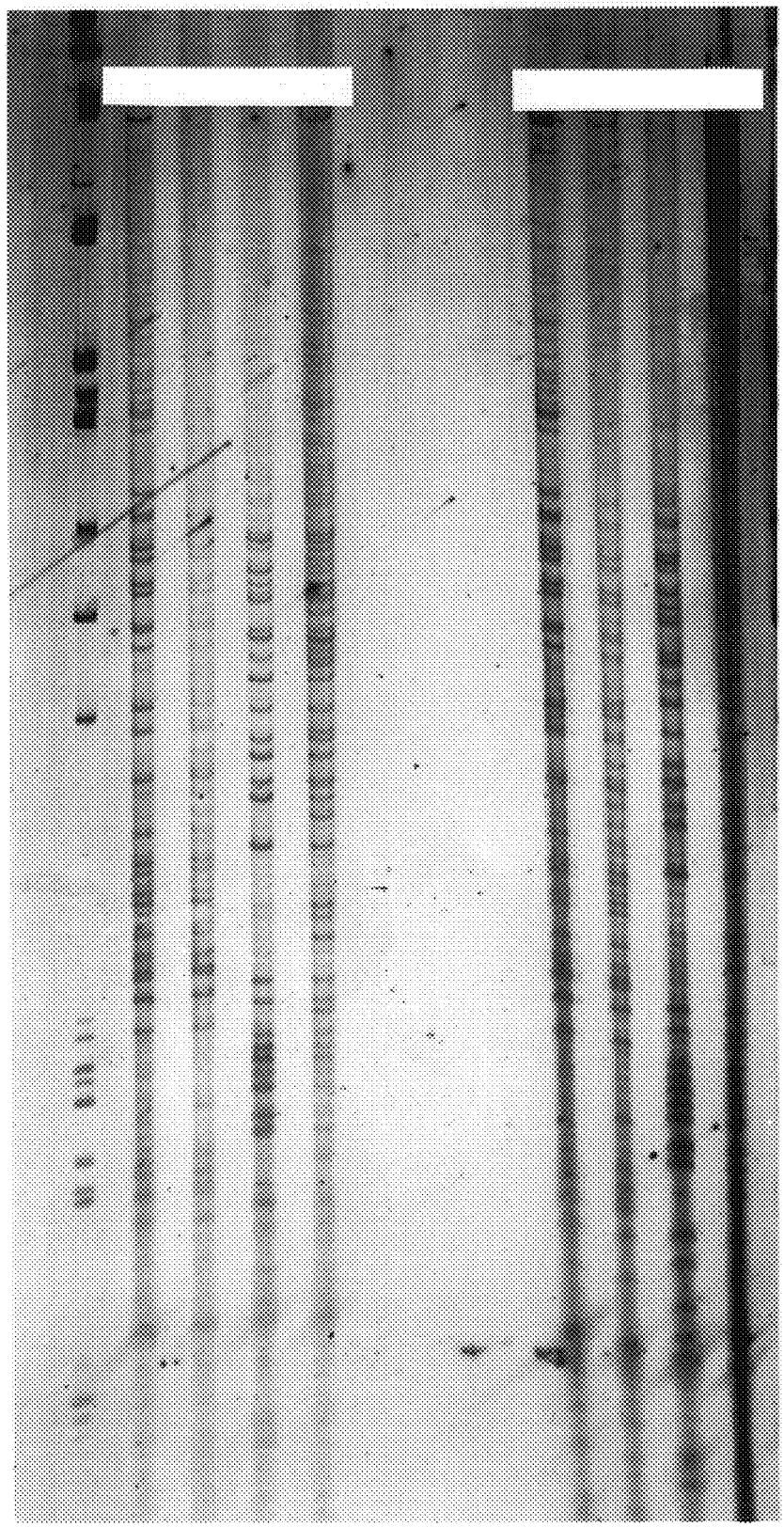
FIG. 3 is the sequence of human p53 (tumor suppressor gene). Exon 5 region was amplified using Polymerase Chain Reaction with one primer labeled with biotin at the 5' end and the amplified product was sequenced using the method described herein. Lanes left to right: 1. pGEM DNA markers; 2. G+A reaction products; 3. G Reaction products; 4. C Reaction products; 5. C+T reaction products; 6. G+A reaction products; 7. G Reaction products; 8. C Reaction products; 9. C+T reaction products; 10. pGEM markers.

For convenience the second strand was shown to be unmodified in the reactions. The results of this sequencing are shown in FIG. 3.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A method of sequencing a nucleic acid comprising:
   a) labeling the nucleic acid with biotin;
   b) subjecting the nucleic acid of step a) to base specific chemical modifications;
   c) cleaving the nucleic acid of step b) at the modified bases with hot piperidine
   d) contacting the nucleic acid of step c) with immobilized streptavidin whereby biotin-containing fragments are bound to immobilized streptavidin and unbound fragments are washed off;
   e) contacting the biotin-containing fragments of d) with sodium hydroxide whereby, the biotin-containing fragments are dissociated into biotin-containing single stranded fragments and their complementary strands;

f) extracting the biotin-containing single stranded fragments of step e);

g) resolving the fragments of step f) on a denaturing polyacrylamide gel; and h) staining the fragments in the gel of step g) by silver staining whereby the nucleic acid sequence is determined.

2. A method of sequencing a nucleic acid comprising:

a) labeling the nucleic acid with DMT (dimethyl trityl protective group);

b) subjecting the nucleic acid of step a) to base specific chemical modifications;

c) cleaving the nucleic acid of step b) at the modified bases wit hot piperidine;

d) contacting the nucleic acid of step c) with an OPC (Oligo Purification Column) whereby DMT-containing fragments are bound to the OPC and unbound fragments are washed off;

e) contacting the DMT-containing fragments of d) with sodium hydroxide or ammonium hydroxide, whereby the DMT-containing fragments are dissociated into DMT- containing single stranded fragments and their complementary strands;

f) eluting the DMT-containing single stranded fragments of step e;

g) resolving the fragments of step f) on a denaturing polyacrylamide gel; and h) staining the fragments in the gel of step g) by silver staining whereby a permanent record of the nucleic acid sequence is provided and whereby the nucleic acid sequence is determined.

* * * * *

SEQUENCE LISTING

```
<160> NUMBER OF SEQ ID NOS: 37

<210> SEQ ID NO 1
<211> LENGTH: 30
<212> TYPE: DNA
<213> ORGANISM: Artificial Sequence
<220> FEATURE:
<223> OTHER INFORMATION: Description of artificial sequence: /Note =
      Template

<400> SEQUENCE: 1
tactcccctg ccctccacaa gatgttttgc                                      30

<210> SEQ ID NO 2
<211> LENGTH: 30
<212> TYPE: DNA
<213> ORGANISM: Artificial Sequence
<220> FEATURE:
<223> OTHER INFORMATION: Description of artificial sequence: /Note =
      Products of the G reaction (Total Products)

<400> SEQUENCE: 2
```
tactcccctg ccctccacaa gatgttttgc                    30

<210> SEQ ID NO 3
<211> LENGTH: 29
<212> TYPE: DNA
<213> ORGANISM: Artificial Sequence
<220> FEATURE:
<223> OTHER INFORMATION: Description of artificial sequence: /Note =
      Products of the G reaction (Total Products)

<400> SEQUENCE: 3
tactcccctg ccctccacaa gatgttttc                     29

<210> SEQ ID NO 4
<211> LENGTH: 29
<212> TYPE: DNA
<213> ORGANISM: Artificial Sequence
<220> FEATURE:
<223> OTHER INFORMATION: Description of artificial sequence: /Note =
      Products of the G reaction (Total Products)

<400> SEQUENCE: 4
tactcccctg ccctccacaa gatttttgc                     29

<210> SEQ ID NO 5
<211> LENGTH: 29
<212> TYPE: DNA
<213> ORGANISM: Artificial Sequence
<220> FEATURE:
<223> OTHER INFORMATION: Description of artificial sequence: /Note =
      Products of the G reaction (Total Products)

<400> SEQUENCE: 5
tactcccctg ccctccacaa atgttttgc                     29

<210> SEQ ID NO 6
<211> LENGTH: 29
<212> TYPE: DNA
<213> ORGANISM: Artificial Sequence
<220> FEATURE:
<223> OTHER INFORMATION: Description of artificial sequence: /Note =
      Products of the G reaction (Total Products)

<400> SEQUENCE: 6
tactcccctc cctccacaag atgttttgc                     29

<210> SEQ ID NO 7
<211> LENGTH: 30
<212> TYPE: DNA
<213> ORGANISM: Artificial Sequence
<220> FEATURE:
<223> OTHER INFORMATION: Description of artificial sequence: /Note =
      Products of G reaction captured by the beads
      (Informative products)

<400> SEQUENCE: 7
tactcccctg ccctccacaa gatgttttgc                    30

<210> SEQ ID NO 8
<211> LENGTH: 28
<212> TYPE: DNA
<213> ORGANISM: Artificial Sequence
<220> FEATURE:
<223> OTHER INFORMATION: Description of artificial sequence: /Note =
      Products of G reaction captured by the beads
      (Informative products)

```
<400> SEQUENCE: 8
tactcccctg ccctccacaa gatgtttt                                              28

<210> SEQ ID NO 9
<211> LENGTH: 23
<212> TYPE: DNA
<213> ORGANISM: Artificial Sequence
<220> FEATURE:
<223> OTHER INFORMATION: Description of artificial sequence: /Note =
      Products of G reaction captured by the beads
      (Informative products)

<400> SEQUENCE: 9
tactcccctg ccctccacaa gat                                                   23

<210> SEQ ID NO 10
<211> LENGTH: 20
<212> TYPE: DNA
<213> ORGANISM: Artificial Sequence
<220> FEATURE:
<223> OTHER INFORMATION: Description of artificial sequence: /Note =
      Products of G reaction captured by the beads
      (Informative products)

<400> SEQUENCE: 10
tactcccctg ccctccacaa                                                       20

<210> SEQ ID NO 11
<211> LENGTH: 9
<212> TYPE: DNA
<213> ORGANISM: Artificial Sequence
<220> FEATURE:
<223> OTHER INFORMATION: Description of artificial sequence: /Note =
      Products of G reaction captured by the beads
      (Informative products)

<400> SEQUENCE: 11 tactcccct                                                                    9

<210> SEQ ID NO 12
<211> LENGTH: 26
<212> TYPE: DNA
<213> ORGANISM: Artificial Sequence
<220> FEATURE:
<223> OTHER INFORMATION: Description of artificial sequence: /Note = Primer

<400> SEQUENCE: 12
ggatccatct gttcacttgt gccctg                                                26

<210> SEQ ID NO 13
<211> LENGTH: 26
<212> TYPE: DNA
<213> ORGANISM: Artificial Sequence
<220> FEATURE:
<223> OTHER INFORMATION: Description of artificial sequence: /Note = Primer

<400> SEQUENCE: 13
gaattcaacc agccctgtcg tctctc                                                26

<210> SEQ ID NO 14
<211> LENGTH: 20
<212> TYPE: DNA
<213> ORGANISM: Artificial Sequence
<220> FEATURE:
<223> OTHER INFORMATION: Description of artificial sequence: /Note =
      Template
```

<400> SEQUENCE: 14
gatcgatcga tcgatcgatc                                          20

<210> SEQ ID NO 15
<211> LENGTH: 20
<212> TYPE: DNA
<213> ORGANISM: Artificial Sequence
<220> FEATURE:
<223> OTHER INFORMATION: Description of artificial sequence: /Note =
      Template

<400> SEQUENCE: 15
ctagctagct agctagctag                                          20

<210> SEQ ID NO 16
<211> LENGTH: 19
<212> TYPE: DNA
<213> ORGANISM: Artificial Sequence
<220> FEATURE:
<223> OTHER INFORMATION: Description of artificial sequence: /Note =
      Products of the G Reaction (Total Products)

<400> SEQUENCE: 16
gatcgatcga tcgatcatc                                           19

<210> SEQ ID NO 17
<211> LENGTH: 20
<212> TYPE: DNA
<213> ORGANISM: Artificial Sequence
<220> FEATURE:
<223> OTHER INFORMATION: Description of artificial sequence: /Note =
      Products of the G Reaction (Total Products)

<400> SEQUENCE: 17
ctagctagct agctagctag                                          20

<210> SEQ ID NO 18
<211> LENGTH: 19
<212> TYPE: DNA
<213> ORGANISM: Artificial Sequence
<220> FEATURE:
<223> OTHER INFORMATION: Description of artificial sequence: /Note =
      Products of the G Reaction (Total Products)

<400> SEQUENCE: 18
gatcgatcga tcatcgatc                                           19

<210> SEQ ID NO 19
<211> LENGTH: 20
<212> TYPE: DNA
<213> ORGANISM: Artificial Sequence
<220> FEATURE:
<223> OTHER INFORMATION: Description of artificial sequence: /Note =
      Products of the G Reaction (Total Products)

<400> SEQUENCE: 19
ctagctagct agctagctag                                          20

<210> SEQ ID NO 20
<211> LENGTH: 19
<212> TYPE: DNA
<213> ORGANISM: Artificial Sequence
<220> FEATURE:
<223> OTHER INFORMATION: Description of artificial sequence: /Note =
      Products of the G Reaction (Total Products)

<400> SEQUENCE: 20

```
gatcgatcat cgatcgatc                                                    19

<210> SEQ ID NO 21
<211> LENGTH: 20
<212> TYPE: DNA
<213> ORGANISM: Artificial Sequence
<220> FEATURE:
<223> OTHER INFORMATION: Description of artificial sequence: /Note =
      Products of the G Reaction (Total Products)

<400> SEQUENCE: 21
ctagctagct agctagctag                                                   20

<210> SEQ ID NO 22
<211> LENGTH: 19
<212> TYPE: DNA
<213> ORGANISM: Artificial Sequence
<220> FEATURE:
<223> OTHER INFORMATION: Description of artificial sequence: /Note =
      Products of the G Reaction (Total Products)

<400> SEQUENCE: 22
gatcatcgat cgatcgatc                                                    19

<210> SEQ ID NO 23
<211> LENGTH: 20
<212> TYPE: DNA
<213> ORGANISM: Artificial Sequence
<220> FEATURE:
<223> OTHER INFORMATION: Description of artificial sequence: /Note =
      Products of the G Reaction (Total Products)

<400> SEQUENCE: 23
ctagctagct agctagctag                                                   20

<210> SEQ ID NO 24
<211> LENGTH: 19
<212> TYPE: DNA
<213> ORGANISM: Artificial Sequence
<220> FEATURE:
<223> OTHER INFORMATION: Description of artificial sequence: /Note =
      Products of the G Reaction (Total Products)

<400> SEQUENCE: 24
atcgatcgat cgatcgatc                                                    19

<210> SEQ ID NO 25
<211> LENGTH: 20
<212> TYPE: DNA
<213> ORGANISM: Artificial Sequence
<220> FEATURE:
<223> OTHER INFORMATION: Description of artificial sequence: /Note =
      Products of the G Reaction (Total Products)

<400> SEQUENCE: 25
ctagctagct agctagctag                                                   20

<210> SEQ ID NO 26
<211> LENGTH: 16
<212> TYPE: DNA
<213> ORGANISM: Artificial Sequence
<220> FEATURE:
<223> OTHER INFORMATION: Description of artificial sequence: /Note =
      Products of the G Reaction captured on the beads

<400> SEQUENCE: 26
```

```
gatcgatcga tcgatc                                                    16
```

<210> SEQ ID NO 27
<211> LENGTH: 20
<212> TYPE: DNA
<213> ORGANISM: Artificial Sequence
<220> FEATURE:
<223> OTHER INFORMATION: Description of artificial sequence: /Note =
      Products of the G Reaction captured on the beads

<400> SEQUENCE: 27

```
ctagctagct agctagctag                                                20
```

<210> SEQ ID NO 28
<211> LENGTH: 12
<212> TYPE: DNA
<213> ORGANISM: Artificial Sequence
<220> FEATURE:
<223> OTHER INFORMATION: Description of artificial sequence: /Note =
      Products of the G Reaction captured on the beads

<400> SEQUENCE: 28

```
gatcgatcga tc                                                        12
```

<210> SEQ ID NO 29
<211> LENGTH: 20
<212> TYPE: DNA
<213> ORGANISM: Artificial Sequence
<220> FEATURE:
<223> OTHER INFORMATION: Description of artificial sequence: /Note =
      Products of the G Reaction captured on the beads

<400> SEQUENCE: 29

```
ctagctagct agctagctag                                                20
```

<210> SEQ ID NO 30
<211> LENGTH: 8
<212> TYPE: DNA
<213> ORGANISM: Artificial Sequence
<220> FEATURE:
<223> OTHER INFORMATION: Description of artificial sequence: /Note =
      Products of the G Reaction captured on the beads

<400> SEQUENCE: 30

```
gatcgatc                                                             8
```

<210> SEQ ID NO 31
<211> LENGTH: 20
<212> TYPE: DNA
<213> ORGANISM: Artificial Sequence
<220> FEATURE:
<223> OTHER INFORMATION: Description of artificial sequence: /Note =
      Products of the G Reaction captured on the beads

<400> SEQUENCE: 31

```
ctagctagct agctagctag                                                20
```

<210> SEQ ID NO 32
<211> LENGTH: 4
<212> TYPE: DNA
<213> ORGANISM: Artificial Sequence
<220> FEATURE:
<223> OTHER INFORMATION: Description of artificial sequence: /Note =
      Products of the G Reaction captured on the beads

<400> SEQUENCE: 32

```
gatc                                                                 4
```

```
<210> SEQ ID NO 33
<211> LENGTH: 20
<212> TYPE: DNA
<213> ORGANISM: Artificial Sequence
<220> FEATURE:
<223> OTHER INFORMATION: Description of artificial sequence: /Note =
      Products of the G Reaction captured on the beads

<400> SEQUENCE: 33
ctagctagct agctagctag                                                     20

<210> SEQ ID NO 34
<211> LENGTH: 16
<212> TYPE: DNA
<213> ORGANISM: Artificial Sequence
<220> FEATURE:
<223> OTHER INFORMATION: Description of artificial sequence: /Note =
      Products of the G Reaction after sodium hydroxide
      treatment

<400> SEQUENCE: 34
gatcgatcga tcgatc                                                         16

<210> SEQ ID NO 35
<211> LENGTH: 12
<212> TYPE: DNA
<213> ORGANISM: Artificial Sequence
<220> FEATURE:
<223> OTHER INFORMATION: Description of artificial sequence: /Note =
      Products of the G Reaction after sodium hydroxide
      treatment

<400> SEQUENCE: 35
gatcgatcga tc                                                             12

<210> SEQ ID NO 36
<211> LENGTH: 8
<212> TYPE: DNA
<213> ORGANISM: Artificial Sequence
<220> FEATURE:
<223> OTHER INFORMATION: Description of artificial sequence: /Note =
      Products of the G Reaction after sodium hydroxide
      treatment

<400> SEQUENCE: 36 gatcgatc                                                                  8

<210> SEQ ID NO 37
<211> LENGTH: 4
<212> TYPE: DNA
<213> ORGANISM: Artificial Sequence
<220> FEATURE:
<223> OTHER INFORMATION: Description of artificial sequence: /Note =
      Products of the G Reaction after sodium hydroxide
      treatment

<400> SEQUENCE: 37 gatc                                                                      4
```